US011597830B2

(12) United States Patent
Zech et al.

(10) Patent No.: US 11,597,830 B2
(45) Date of Patent: Mar. 7, 2023

(54) RADIATION CURABLE COMPOSITION FOR ADDITIVE MANUFACTURING PROCESSES

(71) Applicant: 3M INNOVATIVE PROPERTIES COMPANY, St. Paul, MN (US)

(72) Inventors: Joachim Zech, Kaufering (DE); Hendrik Grupp, Herrsching am Ammersee (DE); Malte Korten, Moorenweis (DE); Ralf Paehl, Melle (DE); Dietmar Blees, Löhne (DE); Gioacchino Raia, Türkenfeld (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 590 days.

(21) Appl. No.: 16/624,806

(22) PCT Filed: May 21, 2018

(86) PCT No.: PCT/IB2018/053575
§ 371 (c)(1),
(2) Date: Dec. 19, 2019

(87) PCT Pub. No.: WO2018/234898
PCT Pub. Date: Dec. 27, 2018

(65) Prior Publication Data
US 2020/0131356 A1    Apr. 30, 2020

(30) Foreign Application Priority Data

Jun. 20, 2017  (EP) .................................... 17176777

(51) Int. Cl.
| | | |
|---|---|---|
| *C08F 20/10* | (2006.01) | |
| *C08F 120/10* | (2006.01) | |
| *C08F 220/10* | (2006.01) | |
| *C08F 2/46* | (2006.01) | |
| *C08F 2/50* | (2006.01) | |
| *C08G 61/04* | (2006.01) | |
| *C08L 33/10* | (2006.01) | |
| *B33Y 70/00* | (2020.01) | |
| *A61K 6/90* | (2020.01) | |
| *B33Y 10/00* | (2015.01) | |
| *B33Y 80/00* | (2015.01) | |
| *C08K 5/00* | (2006.01) | |

(52) U.S. Cl.
CPC ................ *C08L 33/10* (2013.01); *A61K 6/90* (2020.01); *B33Y 70/00* (2014.12); *B33Y 10/00* (2014.12); *B33Y 80/00* (2014.12); *C08K 5/005* (2013.01); *C08K 5/0025* (2013.01); *C08K 5/0041* (2013.01)

(58) Field of Classification Search
CPC ......... C08L 33/10; B33Y 10/00; B33Y 70/00; B33Y 80/00; A61K 6/90; C08K 5/0025; C08K 5/0041; C08K 5/005

USPC ...... 525/330.3, 326.1, 55, 50; 522/189, 184, 522/71, 6, 1; 520/1
See application file for complete search history.

(56) References Cited

U.S. PATENT DOCUMENTS

| | | |
|---|---|---|
| 4,737,593 A | 4/1988 | Ellrich |
| 6,395,124 B1 | 5/2002 | Oxman |
| 6,855,748 B1 | 2/2005 | Hatton |
| 6,936,642 B2 | 8/2005 | Lehmann |
| 7,141,616 B2 | 11/2006 | Hecht et al. |
| 8,236,871 B2 | 8/2012 | Hecht |
| 9,387,056 B2 | 7/2016 | Wachter |
| 2003/0003172 A1 | 1/2003 | Stange |
| 2003/0152888 A1 | 8/2003 | Sun |
| 2004/0170923 A1 | 9/2004 | Steinmann |
| 2007/0205528 A1 | 9/2007 | Patel |
| 2007/0256781 A1 | 11/2007 | Johnson |
| 2008/0287564 A1* | 11/2008 | Klare ...................... C08L 75/16 522/96 |
| 2010/0056661 A1* | 3/2010 | Xu .......................... G03F 7/033 522/71 |
| 2014/0035202 A1 | 2/2014 | Southwell |
| 2014/0072712 A1 | 3/2014 | Xu |
| 2015/0272833 A1* | 10/2015 | Toriyabe ................. A61K 6/61 522/48 |
| 2015/0313687 A1 | 11/2015 | Blees |

FOREIGN PATENT DOCUMENTS

| | | |
|---|---|---|
| CN | 104893224 | 9/2015 |
| JP | 2013-244151 A | 12/2013 |
| WO | WO 2007-140440 | 12/2007 |
| WO | WO 2012-166460 | 12/2012 |
| WO | WO 2014-078537 | 5/2014 |
| WO | WO 2014-130603 | 8/2014 |
| WO | WO 2015/068820 A | 5/2015 |
| WO | WO 2015-073301 | 5/2015 |
| WO | WO 2018-038954 | 3/2018 |

OTHER PUBLICATIONS

International Search report for PCT International Application No. PCT/IB2018/053575 dated Aug. 23, 2018, 5 pages.

* cited by examiner

*Primary Examiner* — Jessica Whiteley
(74) *Attorney, Agent, or Firm* — 3M Innovative Properties Company

(57) ABSTRACT

The invention relates to a radiation curable composition for additive-manufacturing processes, the composition comprising (meth)acrylate component(s) not comprising an urethane moiety having a molecular weight Mw of at least 1,000 as Component A1, photo initiator as Component B, red, yellow or orange dye or combination thereof as Component C, blue dye having a light absorption band in the range of 350 to 420 nm as Component D, and optionally stabilizer as Component E. The invention further relates to a process of producing an elastomeric 3-dim article from the radiation curable composition in an additive-manufacturing process and the obtained elastomeric 3-dim article.

15 Claims, 1 Drawing Sheet

RADIATION CURABLE COMPOSITION FOR ADDITIVE MANUFACTURING PROCESSES

CROSS REFERENCE TO RELATED APPLICATIONS

This application is a national stage filing under 35 U.S.C. 371 of PCT/IB2018/053575, filed May 21, 2018, which claims the benefit of EP Application No. 17176777.5, filed Jun. 20, 2017, the disclosure of which is incorporated by reference in its/their entirety herein.

FIELD OF THE INVENTION

The invention relates to a radiation curable composition which can be used in an additive manufacturing process.

The radiation curable composition is particularly useful for producing transparent and elastomeric 3-dim articles, which can be further used i.a. in the dental and orthodontic field, e.g. for the fixation of brackets.

BACKGROUND

In orthodontic treatments brackets have to be placed exactly onto patients' teeth. A so-called positioning tray can be a helpful tool for this purpose.

Such a positioning tray or transfer tray basically consists of an impression of the patient's jaw with molds at those positions where the brackets are located. So, the brackets can be put into these molds and thus be transferred into the patient's mouth.

When such a tray including the brackets is seated in a patient's mouth, the brackets are automatically exactly positioned on the teeth.

This procedure is described e.g. in the background art section of US2015/0313687A1 (Blees et al.).

These trays are typically manufactured in time consuming procedures starting from models of a patient's mouth onto which the brackets are placed.

It starts with the manufacturing of a model of a patient's jaw and the positioning of brackets on the lingual side of the teeth model.

Then an outer shell is manufactured by applying a spacer over the model and vacuum forming a deep drawing foil over it.

Then the spacer is removed and the outer shell is filled with a transparent heat curable silicone so that the outer shell acts like an impression tray.

Then the outer shell with the mixed silicone paste is seated back onto the model and heat cured.

Figure 1:
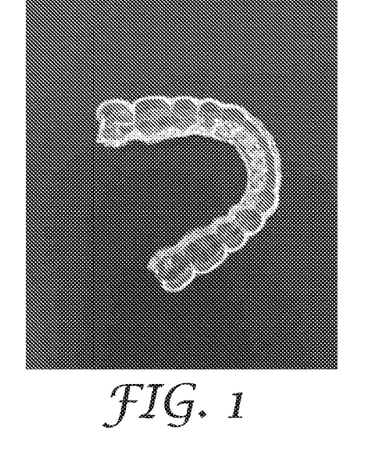
FIG. 1 shows a picture of a clear positioning tray according to the state of the art.

This results in the setting of the silicone which forms an inner shell which is transparent and elastomeric so that it can be processed to take up the brackets. A picture of such a clear positioning tray is shown in FIG. 1.

During use, the clear positioning tray contains all the brackets for a patient's mouth on the lingual sides of the teeth.

In a next step, the clear positioning tray can be used by the orthodontist to seat all the brackets in a patient's jaw at one time which saves time and allows an accurate seating of the brackets.

The brackets typically contain an adhesive or a layer of cement on its surface which can be light cured by the orthodontist.

This means that after seating the clear positioning tray with the brackets in the patient's mouth the practitioner cures the adhesive located on the brackets through the material of the clear positioning tray by using a conventional dental curing light.

The light is applied such that the light shines through the outer and inner shell until the brackets are fixed onto the lingual surfaces of the teeth.

It becomes clear that despite the positive results which can be obtained by following this process, there is a desire for a simplified process.

U.S. Pat. No. 6,855,748 (Hatton) describes UV-curable compositions containing oxetane- and epoxy-compounds in combination with multifunctional hydroxyl-compounds which can contain additional (meth)acrylates and which can be used for laser initiated stereolithographic procedures.

US 2014/0035202 A1 (Southwell et al.) describes radiation curable resin compositions and rapid 3D imaging processes using them. The resins are based on cycloaliphatic epoxides in combination with oxetanes and (meth-)acrylates and cationic and free radical photoinitiators.

One class of suitable free radical photoinitiators comprises the ionic dye-counter ion compounds, which are capable of absorbing actinic rays and producing free radicals.

WO 2014/078537 A1 (Dentsply) describes 3D fabricating material systems for producing dental products like artificial teeth, dentures, splints, veneers, inlays, onlays, copings, frame patterns, crowns, bridges, and the like. DLP procedures are used.

The materials are (meth-)acrylate based and can contain pigments.

WO 2015/073301 A1 (Chang) relates to 3D color printing e.g. by SLA to manufacture 3D-printed pigmented multi-colored parts but does not deal with dyes to avoid overcuring.

US 2007/0205528 A1 (Patel et al.) and US 2007/0256781A1 (Johnson et al.) describe photocurable compositions for rapid prototyping techniques which can contain dyes but they are not dealing with the issue of detail resolution.

WO 2014/078537 A1 (Sun et al.) describes a three-dimensional fabrication material system for producing dental products. The composition for making a three-dimensional dental prosthesis comprises a mixture of (meth) acrylate, an inorganic filler, an organic filler, a silicone-acrylic-based rubber impact modifier, pigments and light initiators.

WO 2013/153183 A2 (Wachter et al.) describes a composite resin composition and method for producing dental components by means of stereo-lithography. The composite resin composition contains a) at least one poly-reactive binder, b) a first photo-polymerization initiator with an absorption maximum at a wavelength of less than 400 nm, c) a second photo polymerization initiator with an absorption maximum of at least 400 nm, and d) an absorber with an absorption maximum at a wavelength of less than 400 nm for the SLA production of a dental formed component on the basis of a composite resin.

US 2008/0287564 A1 (Klare et al.) describes a biocompatible, low-viscosity radiation-curable formulation for producing medical products, in particular adaptive ear pieces, otoplastic parts, shells or ear parts, by means of PNP methods or stereolithographic methods, wherein the critical energy to penetration depth is adjusted by adding small quantities of anaerobic inhibitors such as phenothiazine or DPPH.

US 2014/0072712 A1 (Xu) describes opaque inks for use with a three-dimensional printing system comprising 10-95 wt. % polymerizable component and 3-25 wt. % non-reactive wax component.

US 2010/0056661 A1 (Xu) relates to a radiation-curable composition useful for the production of 3-dim solid articles. The composition comprises a hyperbranched poly (meth)acylate compound, a light sensitizer and an initiator. UV light sensitizers containing a thioxanthone moiety are said to be preferred. The composition may also contain pigments as additives.

US 2004/0170923 A1 (Steinmann et al.) describes a liquid colored radiation-curable composition comprising a cationically polymerizing organic substance, a free-radical polymerizing organic substance, a cationic polymerization initiator, a free-radical polymerization initiator and an effective color-imparting amount of a soluble dye selected from diarylmethane and triarylmethane dyes, rhodamine dyes, azo dyes, thiazole dyes, anthrachinone dyes and safranine dyes. The resin composition is said to be particularly useful in the jewelry industry which require good color contrast in thin layers.

DESCRIPTION OF THE INVENTION

There is a need for a radiation curable composition which can be processed in an additive-manufacturing technique (in particular using a stereolithographic 3d-printing process) to obtain a transparent elastomeric 3dim-article having high surface resolution.

In particular, the radiation curable composition should be suitable to produce an elastomeric 3dim-article, which can be used in the dental or orthodontic field.

Further, sometimes it is desirable to enhance the possibility of inspecting and/or controlling the production of the 3dim-article during the 3d-printing process.

Further, if possible, the radiation curable composition should enable the production of a so-called clear positioning tray (CPT) from data obtained from e.g. an intraoral scan of the dental situation in the mouth of a patient.

Such a clear positioning tray should be sufficient elastic, translucent in particular in the region from 420 to 500 nm and should be easy to remove from other dental or orthodontic appliances and materials, like dental adhesive or dental cement compositions containing (meth)acrylate components.

One or more of the above described objects can be achieved by the invention described in the present text.

In one embodiment, the invention features a radiation curable Composition I as described in the claims and the present text, the composition comprising
- (meth)acrylate component(s) not comprising a urethane moiety, the (meth)acrylate component(s) preferably having a molecular weight Mw of at least 1,000,
- photo initiator,
- red, orange, yellow dye or combination thereof,
- blue dye showing an absorption band in the range of 350 to 420 nm,
- optionally stabilizer.

In another embodiment, the invention relates to a process of producing a transparent, elastomeric 3-dim article as described in the claims and the present text by processing the radiation curable Composition I in an additive-manufacturing process comprising a radiation curing step.

The invention also relates to a transparent, elastomeric 3-dim article obtained by radiation curing the radiation curable Composition I as described in the claims and the present text.

A further aspect of the invention relates to a kit of parts comprising the radiation curable Composition I and a radiation curable Composition II as described in the claims and the present text.

The invention also deals with a process of curing the radiation curable Composition B by irradiating light through a cured elastomeric 3-dim article obtained from the radiation curable Composition I.

Unless defined differently, for this description the following terms shall have the given meaning:

A "hardenable component or material" or "polymerizable component" is any component which can be cured or solidified in the presence of a photo initiator by radiation-induced polymerization. A hardenable component may contain only one, two, three or more polymerizable groups. Typical examples of polymerizable groups include unsaturated carbon groups, such as a vinyl group being present i.a. in a (methyl)acrylate group.

A "photo initiator" is a substance being able to start or initiate the curing process of a hardenable composition in the presence of radiation, in particular light (wave length from 300 to 700 nm).

A "monomer" is any chemical substance which can be characterized by a chemical formula, bearing polymerizable groups (including (meth)acrylate groups) which can be polymerized to oligomers or polymers thereby increasing the molecular weight. The molecular weight of monomers can usually simply be calculated based on the chemical formula given.

As used herein, "(meth)acryl" is a shorthand term referring to "acryl" and/or "methacryl". For example, a "(meth) acryloxy" group is a shorthand term referring to either an acryloxy group (i. e., $CH_2=CH—C(O)—O—$) and/or a methacryloxy group (i. e., $CH_2=C(CH_3)—C(O)—O—$).

A "curing, hardening or setting reaction" is used interchangeable and refers to a reaction wherein physical properties such as viscosity and hardness of a composition changes over the time due to a chemical reaction between the individual components.

The term "dental or orthodontic article" means any article which is to be used in the dental or orthodontic field, especially for producing a dental restoration, orthodontic devices, a tooth model and parts thereof.

Examples of dental articles include crowns, bridges, inlays, onlays, veneers, facings, copings, crown and bridged framework, implants, abutments, dental milling blocks, monolithic dental restorations and parts thereof.

Examples of orthodontic articles include brackets, buccal tubes, cleats and buttons and parts thereof.

A dental or orthodontic article should not contain components which are detrimental to the patient's health and thus free of hazardous and toxic components being able to migrate out of the dental or orthodontic article.

A "transparent article" is an article being transparent if inspected with the human eye, in particular an article which has a light transmission of at least 40% for a path length of 1 mm for light having a wave length of 500 nm.

So, a picture can be seen through a platelet (1 mm thick) of such a transparent material.

A "red dye" is a dye which has a red colour appearance for the human eye.

A "yellow dye" is a dye which has a yellow colour appearance for the human eye.

An "orange dye" is a dye which has an orange colour appearance for the human eye.

"Additive manufacturing" or "3d printing" means processes comprising a radiation curing step used to make 3-dimensional articles. An example of an additive manufacturing technique is stereolithography (SLA) in which successive layers of material are laid down under computer control. The articles can be of almost any shape or geometry and are produced from a 3-dimensional model or other electronic data source.

"Ambient conditions" mean the conditions which the composition described in the present text is usually subjected to during storage and handling. Ambient conditions may, for example, be a pressure of 900 to 1100 mbar, a temperature of 10 to 40° C. and a relative humidity of 10 to 100%. In the laboratory, ambient conditions are typically adjusted to 20 to 25° C. and 1000 to 1025 mbar.

A composition is "essentially or substantially free of" a certain component, if the composition does not contain said component as an essential feature. Thus, said component is not wilfully added to the composition either as such or in combination with other components or ingredient of other components. A composition being essentially free of a certain component usually does not contain that component at all. However, sometimes the presence of a small amount of the said component is not avoidable e.g. due to impurities contained in the raw materials used.

As used herein, "a", "an", "the", "at least one" and "one or more" are used interchangeably. The terms "comprise" or "contain" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about".

The term "comprise" shall include also the terms "consist essentially of" and "consists of".

DETAILED DESCRIPTION

It has been found that the composition described in the text has a couple of advantageous properties.

The radiation curable Composition I described in the present text can be processes as manufacturing material in an additive-manufacturing process, in particular a so-called SLA process.

Due to the presence of a red, orange or yellow dye, in particular a fluorescent dye, the production of the 3-dim article during the additive manufacturing process can easily be inspected, e.g. by using blue light.

Further, the radiation curable Composition I described in the present text helps to solve different problems.

In an additive-manufacturing process, in particular in an SLA process the problem of "overcuring" must be solved. This means that the detail accuracy of the light induced polymerization may not be satisfactory due to the fact, that polymerization does not exactly only take place in the area which is exposed to light but in a somewhat broader area resulting in a loss of detail accuracy in the additive-manufacturing process.

It was found that the use of a red, orange or yellow dye in combination with a blue dye as described in the present text contributes to a good printing accuracy in the additive-manufacturing process resulting in a colored elastomeric article with good detail resolution.

Such an elastomeric article should also be sufficiently transparent to allow the transmission of light in the wave length range which is typically used in the dental field for curing radiation curable dental adhesives or dental cements.

This is particularly useful in the orthodontic field as it enables the radiation of dental adhesives or dental cements being located on the surface of e.g. orthodontic brackets which may be located in a clear positioning tray.

The combination of a blue dye and a further dye selected from a red dye, orange dye and/or yellow dye as suggested in the present text addresses this need, as well.

The elastomeric article obtained by curing the radiation curable Composition I described in the present text is sufficiently transparent in the wave length range of 420 to 500 nm.

Further, the elastomer obtained after curing of the radiation curable Composition I and used for radiation curing another radiation curable composition should be easy to remove from the other radiation curable composition after curing.

It was also found, that the elastomeric 3-dim article obtained from the curable composition described in the present text does not stick to surfaces of other (meth)acrylate containing compositions. That is, the elastomeric 3-dim article can be easily removed from the surface of (meth) acrylate composite articles or compositions, including dental adhesives and dental cements.

This is surprising as both articles, the elastomeric 3-dim article and the (meth)acrylate composite article, are based on the same crosslinking chemistry.

Instead, one would have expected that the curing of a radiation curable (meth)acrylate composition being located on the surface of another (meth)acrylate article will result in an adhesion of that radiation curable (meth)acrylate composition to the other (meth)acrylate article.

According to a preferred embodiment, the invention allows the light-curing of dental compositions like adhesives or cements by irradiating light through the elastomeric transparent 3-dim article obtained by curing the radiation curable Composition I described in the present text and the removing of the elastomeric transparent 3-dim article afterwards.

To our knowledge up to now there are no 3d-printable SLA resins commercially available which show good elastomeric properties after the additive-manufacturing process, like e.g. good elastic recovery and good elongation at brake.

Thus, the radiation curable Composition I described in the present text is in particular useful for fabricating clear positioning trays. Clear positioning trays can now be produced with less efforts.

Further, apart from the use in the orthodontic or dental field, the invention provides a solution for any procedure in which a 3d-printable composition is desired through which a light curing process should be done in order to e.g. shape, fix or cure any part in a manufacturing process chain.

The transparent, elastomeric 3d-printed articles obtained from the radiation curable Composition I described in the present text may also be used for producing technical parts like fittings, shock absorbers, seals, etc.

The invention is directed to the radiation curable Composition I for use in an additive manufacturing process comprising a radiation curing step.

In certain embodiments, the radiation curable Composition I described in the present text typically fulfils the following properties alone or in combination:
a) viscosity: less than 200 Pa*s at 23° C.;
b) pH value: 6 to 8, e.g. if the curable composition is brought in contact with wet pH sensitive paper;
c) light transmission: at least 40% for a path length of 1 mm using light having a wave length of 500 nm;
d) radiation curable with light having a wavelength in the range of 350 to 420 nm;
e) appearance: transparent;
f) color: red, orange or yellow.

In certain embodiments, the combination of the following features is sometimes desirable: a), c) and d) or e) and f).

The radiation curable Composition I described in the present text comprises one or more (meth)acrylate components not comprising an urethane moiety as Component A1.

The nature and structure of Component A1 is not particularly limited unless the desired result cannot be achieved.

Component A1 can be characterized by the following features alone or in combination:
a) comprising at least 2 or 3 or 4 (meth)acrylate moieties;
b) comprising a polyalkylene oxide backbone;
c) molecular weight (Mw): from 1,000 to 20,000 g/mol; or from 2,000 to 15,000 g/mol; or from 3,000 to 10,000 g/mol;
d) comprising a polyether backbone to which (meth)acrylate moieties are attached;
e) viscosity: from 0.1 to 100 Pa*s or 1 to 50 Pa*s at 23° C.

A combination of the features a) and b) or a), b) and c), or a), d) and e) can sometimes be preferred.

According to one embodiment Component A1 comprises a polyalkylene oxide backbone to which at least two (meth) acrylate moieties are attached.

Such a component is suitable for producing a rubber-elastic composition.

The average molar weight (Mw) of Component A1 is typically within a range from 1,000 to 20,000.

A molecular weight in this range may help to improve properties like elasticity, elongation at break, Young's modules and/or elastic modulus.

Suitable methods in the measurement of the molar mass of reactive terminal groups, for example OH group-containing polyalkylene oxides, include the titration of the terminal groups.

Preferred representatives of Component A1 include with:
n=1 to 6, preferably 1 to 4, in particular 1,
m=1 to 6, preferably 1 to 4, in particular 3,
k, l=2 to 500, preferably 4 to 250, in particular 10 to 200,
R',R"=independently selected from H, methyl, ethyl, preferably R'=R"=H,
R=CH$_2$=CH—C(O)—O— or CH$_2$=C(CH$_3$)—C(O)—O—, the bracketed expressions indexed by the symbols k and l being able to be arranged regularly or irregularly alternating or in block form.

Appropriate polyethers or polyether groups which may form the polyalkylene oxide backbone of Component A1 can be produced in a manner known to the person skilled in the art e.g. by the reaction of a starting compound having a reactive hydrogen atom with alkylene oxides, for example ethylene oxide, propylene oxide, butylene oxide, styrene oxide, tetrahydrofurane or epichlorohydrine or mixtures of two or more thereof.

Especially suitable are polyether compounds which are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

The reaction products of low-molecular-weight polyfunctional alcohols having at least two hydroxyl groups with alkylene oxides, so-called polyethers, may also be used as polyols. The alkylene oxides preferably have from 2 to 4 carbon atoms. Suitable polyols are, for example, the reaction products of ethylene glycol, propylene glycol, butanediol or hexanediol isomers with one or more of the following alkylene oxides: ethylene oxide, propylene oxide or butylene oxides like tetrahydrofurane. Furthermore, the reaction products of polyfunctional alcohols such as glycerol, trimethylolethane or trimethylolpropane, pentaerythritol or sugar alcohols, or mixtures of two or more thereof, with the mentioned alkylene oxides, forming polyether polyols are also suitable.

Suitable starting compounds are, for example, water, ethylene glycol, 1,2- or 1,3-propylene glycol, 1,4- or 1,3-butylene glycol, 1,6-hexanediol, 1,8-octanediol, neopentyl glycol, 1,4-hydroxymethylcyclohexane, 2-methyl-1,3-propanediol, glycerol, trimethylolpropane, 1,2,6-hexanetriol, 1,2,4-butanetriol, trimethylolethane, pentaerythritol, mannitol, sorbitol, or mixtures of two or more thereof.

Especially suitable are polyether compounds as are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

For example, polyether polyols which are prepared by copolymerisation of tetrahydrofuran and ethylene oxide in a molar ratio of from 10:1 to 1:1, preferably to 4:1, in the presence of strong acids, for example boron fluoride etherates, are suitable as well.

Specific examples of Component A1 include (meth)acrylated ethylene oxide, propylene oxide, ethylene/propylene oxide copolymers, ethylene oxide/tetrahydrofuran copolymers, polypropylene glycol and mixtures thereof.

Component A1 is typically present in the following amounts:
Lower limit: at least 50 or at least 55 or at least 60 wt. %;
Upper limit: utmost 95 or utmost 90 or utmost 85 wt. %;
Range: from 50 to 95 or from 55 to 90 or from 60 to 85 wt. %;
wt. % with respect to the whole composition.

According to one embodiment, the radiation curable Composition I further comprises (meth)acrylate components with an urethane moiety as Component A2.

Adding a (meth)acrylate components with an urethane moiety may help to improve physical properties of the cured composition like flexural strength and/or elongation at break.

Component A2 can be characterized by the following features alone or in combination:

a) comprising at least 2 or 3 or 4 (meth)acrylate moieties;
b) molecular weight (Mw): from 200 to 1,000 g/mol or from 300 to 800 g/mol;
c) comprising a $C_1$ to $C_{20}$ linear or branched alkyl moiety to which the (meth)acrylate moieties are attached through urethane moieties;
d) viscosity: from 0.1 to 100 Pa*s or 1 to 50 Pa*s at 23° C.

A combination of the features a) and b) or b) and c) or a) and d) can sometimes be preferred.

Urethane (meth)acrylates may be obtained by a number of processes known to the skilled person.

The urethane(meth)acrylates are typically obtained by reacting an NCO-terminated compound with a suitable monofunctional (meth)acrylate monomer such as hydroxyethyl acrylate, hydroxyethyl methacrylate, hydroxypropylmethacrylate, preferably hydroxyethyl- and hydroxypropylmethacrylate.

For example, a polyisocyanate and a polyol may be reacted to form an isocyanate-terminated urethane prepolymer that is subsequently reacted with a (meth)acrylate such as 2-hydroxy ethyl(meth)acrylate. These types of reactions may be conducted at room temperature or higher temperature, optionally in the presence of catalysts such as tin catalysts, tertiary amines and the like.

Polyisocyanates which can be employed to form isocyanate-functional urethane prepolymers can be any organic isocyanate having at least two free isocyanate groups. Included are aliphatic cycloaliphatic, aromatic and araliphatic isocyanates.

Any of the known polyisocyanates such as alkyl and alkylene polyisocyanates, cycloalkyl and cycloalkylene polyisocyanates, and combinations such as alkylene and cycloalkylene polyisocyanates can be employed.

Preferably, diisocyanates having the formula $X(NCO)_2$ can be used, with X representing an aliphatic hydrocarbon radical with 2 to 12 C atoms, a cycloaliphatic hydrocarbon radical with 5 to 18 C atoms, an aromatic hydrocarbon radical with 6 to 16 C atoms and/or an araliphatic hydrocarbon radical with 7 to 15 C atoms.

Examples of suitable polyisocyanates include 2,2,4-trimethylhexamethylene-1,6-diisocyanate, hexamethylene-1,6-diisocyanate (HDI), cyclohexyl-1,4-diisocyanate, 4,4'methylene-bis(cyclohexyl isocyanate), 1,1'-methylenebis(4-isocyanato) cyclohexane, isophorone diisocyanate, 4,4'-methylene diphenyl diisocyanate, 1,4-tetramethylene diisocycanate, meta- and para-tetramethylxylene diisocycanate, 1,4-phenylene diisocycanate, 2,6- and 2,4-toluene diisocycanate, 1,5-naphthylene diisocycanate, 2,4' and 4,4'-diphenylmethane diisocycanate and mixtures thereof.

It is also possible to use higher-functional polyisocyanates known from polyurethane chemistry or else modified polyisocyanates, for example containing carbodiimide groups, allophanate groups, isocyanurate groups and/or biuret groups. Particularly preferred isocyanates are isophorone diisocyanate, 2,4,4-trimethyl-hexamethylene diisocyanate and higher-functional polyisocyanates with isocyanurate structure.

The isocyanate terminated urethane compound is capped with a (meth)acrylate to produce a urethane(meth)acrylate compound. In general, any (meth)acrylate-type capping agent having a terminal hydroxyl group and also having an acrylic or methacrylic moiety can be employed, with the methacrylic moiety being preferred.

Examples of suitable capping agents include 2-hydroxyethyl(meth)acrylate, 2-hydroxypropyl (meth)acrylate, glycerol di(meth)acrylate and/or trimethylolpropane di(meth)acrylate. Particularly preferred are 2-hydroxyethyl methacrylate (HEMA) and/or 2-hydroxyethyl acrylate (HEA).

The equivalence ratio of isocyanate groups to compounds reactive vis-à-vis isocyanate groups is 1.1:1 to 8:1, preferably 1.5:1 to 4:1.

The isocyanate polyaddition reaction can take place in the presence of catalysts known from polyurethane chemistry, for example organotin compounds such as dibutyltin dilaurate or amine catalysts such as diazabicyclo[2.2.2]octane. Furthermore, the synthesis can take place both in the melt or in a suitable solvent which can be added before or during the prepolymer preparation. Suitable solvents are for example acetone, 2-butanone, tetrahydrofurane, dioxane, dimethylformamide, N-methyl-2-pyrrolidone (NMP), ethyl acetate, alkyl ethers of ethylene and propylene glycol and aromatic hydrocarbons. The use of ethyl acetate as solvent is particularly preferred.

Suitable examples of urethane (meth)acrylates include 7,7,9-trimethyl-4,13-dioxo-3,14-dioxa-5,12-diazahexadecane-1,16-dioxy-dimethacrylate (e.g. Plex 666-1, Röhm), 7,7,9-trimethyl-4,13-dioxo-5,12-diazahexadecane-1,16-dioxy-dimethacrylate (UDMA), urethane (methacrylates) derived from 1,4 and 1,3-Bis(1-isocyanato-1-methylethyl) benzene (e.g. as described in EP 0934926 A1) and mixtures thereof.

A suitable urethane dimethacrylate can be characterized e.g. by the following formula:

where $R^1$ is a hydrogen atom or a methyl group, and $R^2$ is a linear or branched alkylene group of 1 to 8 carbon atoms or Specific examples of Component A2 also include di(acryloxyethyl)dimethylene diurethane, di(methacryloxyethyl)-dimethylene diurethane, di(acryloxyethyl)tetramethylene diurethane, di(methacryloxyethyl)-tetramethylene diurethane, di(acryloxyethyl)-trimethylhexamethylene diurethane, and di(methcryloxyethyl)-trimethylhexanmethylene diurethane, and mixtures thereof.

According to one embodiment the urethane dimethacrylate of the following formula is preferred:

$$H_2C=C(CH_3)-COO-CH_2-CH_2-OCO-NH-C(CH_3)H-CH_2-C(CH_3)H-CH(H_2)-C(H_2)H-C(H_2)-N H-COO-CH_2-CH_2-OCO-C(CH_3)=CH_2$$

Other suitable urethane(meth)acrylates which may be present in the radiation curable composition described in the present text are characterized as follows:
having the structure A-(—S1-U—S2-MA)$_n$, with
A being a connector element comprising at least one unit,
S1 being a spacer group comprising at least 4 units connected with each other,
S2 being a spacer group comprising at least 4 units connected with each other,
the units of A, S1 and S2 being independently selected from $CH_3-$, $-CH_2-$, $-O-$, $-S-$, $-NR^1-$, $-CO-$, $-CR^1=$

[structures shown]

$-N=$, $-CR^1R^2-$,
with $R^1$ and $R^2$ being independently selected from hydrogen, alkyl, substituted alkyl, alkenyl, cycloalkyl, substituted cycloalkyl, arylalkyl, aryl or substituted aryl, wherein these units can form linear, branched or cyclic structures such as alkyl, cycloalkyl, aryl, ester, urethane or amide groups,
U being a urethane group connecting spacer groups S1 and S2,
MA being an acrylate or methacrylate group and
n being 3 to 6.
According to one embodiment the urethane(meth)acrylate is represented by the structure A-(—S1-U—S2-MA)$_n$ with
A being a connector element comprising at least 1, 2, 3, 4, 5, 6, 7, 8, 9, 10, 11, 12, 13, 14, 15, 16, 17, 18, 19 or 20 units,
S1 being a spacer group comprised of units connected with each other and comprising at least 4, 5, 6, 7, 8, 9 or 10 units,
S2 being a spacer group comprised of units connected with each other and comprising at least 4, 5, 6, 7, 8, 9, 10, 12, 15, 20 or 25 units,
U being a urethane group connecting spacer groups S1 and S2,
MA being an acrylate or methacrylate group and
n being 3 to 6 or 4 to 6 or 5 to 6.
It can be preferred, if A has a cyclic structure and comprises at least 6 units.
It can further be preferred, if S1 has a linear or branched structure and comprises at least 4 or 6 units.
It can further be preferred, if S2 has a linear or branched structure and comprises at least 6 or 8 units.

A urethane(meth)acrylate wherein A has a cyclic structure and comprises at least about 6 units and S1 has a linear structure and comprises at least 4 units and S2 has a linear structure and comprises at least 8 units and U is a urethane group can also be preferred.

Neither the atoms of the urethane group connecting S1 and S2 nor the atoms of the (meth)acryl group belong to the spacer group S1 or S2. Thus, the atoms of the urethane group do not count as units of the spacer groups S1 or S2.

The nature and structure of the connector element is not particularly limited. The connector element can contain saturated (no double bonds) or unsaturated (at least one or two double bonds) units, aromatic or hetero aromatic units (aromatic structure containing atoms including N, O and S).

Specific examples of connector element A having a cyclic structure include:

(6 units)  (6 units)

Specific examples of connector element A having a non-cyclic but branched structure include:

(5 units)  (1 unit)

(16 units)

The dotted lines indicate the bondings to the spacer group S1.

The nature and structure of the spacer groups S1 or S2 is not particularly limited, either.

The spacer groups are comprised of units connected with each other. Typical units include: $CH_3-$, $-CH_2-$, $-O-$, $-S-$, $-NR^1-$, $-CO-$, $-CR^1=$, $N=$, $-CR^1R^2-$, with $R^1$ and $R^2$ independently selected from hydrogen, alkyl, substituted alkyl, alkenyl, cycloalkyl, substituted cycloalkyl, arylalkyl, aryl or substituted aryl.

These units can form linear, branched or cyclic structures such as alkyl, cycloalkyl, aryl, ester, urethane or amide groups.

The structure of S1 can be identical to the structure of S2. However, in some embodiments the structure of S1 is different from S2. In a specific embodiment the number of units being present in S1 is less or equal than the number of units being present in S2.

In a specific embodiment, S1 may have a saturated hydrocarbon structure.

In another specific embodiment, S2 may have a saturated hydrocarbon structure.

Typical examples of useful spacer groups for S1 include:

(13 units)

(13 units)

(8 units)

(8 units)

The dotted lines indicate the chemical bonding to either the group A or the group U.

Typical examples of useful spacer groups for S2 include:

(9 units)

(16 units)

(6 units)

The dotted lines indicate the chemical bonding to either the (meth)acrylate group or the group U. The number of the units to be counted according to the invention is given in brackets.

Specific examples of hardenable component (B) include

Further suitable urethane(meth)acrylates are based on α,ω-terminated poly(meth)acrylatdiols (e.g. as described in EP 1 242 493 B1) or can be a polyester, polyether, polybutadiene or polycarbonate urethane(meth)acrylate (e.g. as described in U.S. Pat. No. 6,936,642 B2).

If present, Component A2 is typically present in the following amounts:
  Lower limit: at least 1 or at least 5 or at least 10 wt. %;
  Upper limit: utmost 40 or utmost 35 or utmost 30 wt. %;
  Range: from 1 to 40 or from 5 to 35 or from 10 to 30 wt. %;
wt. % with respect to the whole composition.

According to one embodiment, the radiation curable composition comprises Component(s) A1 and Component(s) A2, wherein Component(s) A1 is present in excess over Components(s) A2.

The molecular weight of Component A2 is typically lower than the molecular weight of Component A1.

The radiation curable Composition I described in the present text comprises one or more photoinitiator(s) as Component B.

The nature and structure of the photoinitiator is not particularly limited, either, unless the desired result cannot be achieved.

The photo initiator(s) can typically be characterized by one or more of the following features:
  showing a light absorption band in a wave length range from 300 to 450 nm, preferably in the range from 380 to 420 nm;
  solubility: at least 2 g in 100 g of triethylenglycoldi(meth)acrylate (TEGDMA) at 23° C.

The photo initiator typically absorbs light in the blue spectral range, e.g. in the range from 350 to 450 nm.

The photo initiator should be soluble in the radiation curable components of the curable resin composition described in the present text.

The photo initiator is capable of generating free radicals for polymerization upon exposure to light energy having a wavelength between 350 and 450 nm.

The following class of photoinitiator(s) was found to be particular useful: one component system where two radicals are generated by cleavage.

Examples of photoinitiators according to this type) typically contain a moiety selected form benzoin ether, acetophenon, benzoyl oxime or acyl phosphine.

A particularly suitable class of photo initiators include the class of acylphosphine oxides, as described e.g. in U.S. Pat. No. 4,737,593 (Elrich et al.).

Such acylphosphine oxides are of the general formula wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S—, O-, or N-containing five- or six-membered heterocyclic group, or a —Z—C(=O)—P(=O)— $(R^9)_2$ group, wherein Z represents a divalent hydrocarbyl group such as alkylene or phenylene having from 2 to 6 carbon atoms.

Preferred acylphosphine oxides are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms.

Exemplary UV initiators include 1-hydroxycyclohexyl benzophenone (available, for example, under the previous trade designation "IRGACURE™ 184" from Ciba Specialty Chemicals Corp., Tarrytown, N.Y.), 4-(2-hydroxyethoxy) phenyl-(2-hydroxy-2-propyl) ketone (available, for example, under the previous trade designation "IRGACURE™ 2529" from Ciba Specialty Chemicals Corp.), 2-hydroxy-2-methylpropiophenone (available, for example, under the previous trade designation "DAROCURE™ D111" from Ciba Specialty Chemicals Corp. and bis(2,4,6-trimethylbenzoyl)-phenylposphineoxide (available, for example, under the previous trade designation "IRGACURE™ 819" from Ciba Specialty Chemicals Corp.).

Most preferably, the acylphosphine oxide is bis(2,4,6-trimethylbenzoyl)phenyl phosphine oxide (previously known as IRGACURE™ 819, Ciba Specialty Chemicals, Tarrytown, N.Y.).

Tertiary amine reducing agents may be used in combination with an acylphosphine oxide. Illustrative tertiary amines include ethyl 4-(N,N-dimethylamino)benzoate and N,N-dimethylaminoethyl methacrylate.

Commercially-available phosphine oxide photoinitiators capable of free-radical initiation when irradiated at wavelengths of greater than 400 nm to 1200 nm include a 25:75 mixture, by weight, of bis(2,6-dimethoxybenzoyl)-2,4,4- trimethylpentyl phosphine oxide and 2-hydroxy-2-methyl-1-phenylpropan-1-one (previously available as IRGACURE™ 1700, Ciba Specialty Chemicals), 2-benzyl-2-(N,N-dimethylamino)-1-(4-morpholinophenyl)-1-butanone (previously available as IRGACURE™ 369, Ciba Specialty Chemicals), bis(η5-2,4-cyclopentadien-1-yl)-bis(2,6-difluoro-3-(1H-pyrrol-1-yl)phenyl) titanium (previously available as IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenyl-propane-1-one (previously available as DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

Also useful are photoinitiators comprising an alpha, beta-triketon moiety or comprising an alpha-diketon dialkyl ketal moiety.

The photoinitiator(s) is typically present in the following amounts:
  Lower amount: at least 0.01 or at least 0.05 or at least 0.1 wt. %;
  Upper amount: at most 5 or at most 3 or at most 2 wt. %;
  Range: from 0.01 to 5 or from 0.01 to 3 wt. % or 0.01 to 2 wt. %;
  wt. % with respect to the weight of the whole composition.

The radiation curable composition described in the present text comprises one or more red, orange, yellow dye(s) or combinations thereof as Component C.

The nature and structure of Component C is not particularly limited unless the desired result cannot be achieved.

The red dye has a light absorption band, preferably shows a light absorption maximum, within a wave length range from 550 to 600 nm.

The orange dye has a light absorption band, preferably shows a light absorption maximum, within a wave length range from 480 to 550 nm.

The yellow dye has a light absorption band, preferably shows a light absorption maximum, within a wave length range from 460 to 480 nm.

The dye may also be a red, orange or yellow fluorescent dye, i.e. a dye showing fluorescence if irradiated with light.

According to one embodiment, Component C is characterized by the following features alone or in combination:
a) solubility: at least 0.1 g in 100 g triethylenglycoldi(meth)acrylate (TEGDMA) at 23° C.;
b) having a light absorption band in the range of 460 to 600 nm;
c) having a fluorescence band in the range of 500 to 650 nm;
d) comprising a perylene moiety.

A combination of the features a) and b) or a), b) and c) or a), b), c) and d) can sometimes be preferred.

Adding a red, orange or yellow dye as described in the present text may help to improve the printing accuracy, in particular as regards the surface details.

Further, it can be advantageous if the red, orange or yellow dye absorb light in the range from 380 to 420 nm. Such a light absorption may further contribute to a good printing accuracy.

In particular the presence of a dye showing fluorescence in the spectrum visible to the human eye allows an easy inspection and control of the 3-dim article during an additive manufacturing process, in particular an SLA process.

Suitable examples for the red dye include Lumogen™ F Red 300 (BASF) and Fluoreszenzrot 94720 (Kremer) having an absorption maximum at 575 nm.

A suitable example for an orange dye is Fluoreszenzorange 94738 (Kremer) having an absorption maximum at 526 nm.

A suitable example for a yellow dye is Fluoreszenzgelb 94700 (Kremer) having an absorption maximum at 474 nm.

The red dye is typically present in the following amount(s):
  Lower limit: at least 0.001 or at least 0.003 or at least 0.005 wt. %;
  Upper limit: utmost 1 or utmost 0.5 or utmost 0.1 wt. %;
  Range: from 0.001 to 1 or from 0.003 to 0.5 or from 0.005 to 0.1 wt. %;
  wt. % with respect to the whole composition.

The radiation curable composition described in the present text comprises one or more blue dye(s) as Component D.

The nature and structure of Component D is not particularly limited, either unless the desired result cannot be achieved.

The blue dye may also be a blue fluorescent dye, i.e. a red dye showing fluorescence if irradiated with light.

The blue dye has light absorption band, preferably shows a light absorption maximum, within a wave length range from 350 to 420 nm.

If desired, the blue dye can be further characterized by at least one or more of the following features:
a) solubility: at least 0.1 g in 100 g TEGMA at 23° C.;
b) having a light absorption band within a wave length range from 350 to 420 nm;
c) having a fluorescence band in the range of 440 to 550 nm;
d) not having a light absorption band in the wave length range from 440 to 500 nm;
e) comprising a terephthalate moiety.

A combination of the features a) and b) or a), b) and c) can sometimes be preferred.

The blue dye typically has a light absorption band within a wave length range from 300 to 450 nm, that is, in a range relating to the UV region.

Such an absorption can be advantageous as it corresponds or overlaps essentially with the emission band(s) of the light of the devices which are used for the additive manufacturing technique.

Typically, the blue dye shows a light absorption band in the same region of the electromagnetic spectrum where the photo initiator shows light absorption as well.

The blue dye is typically soluble in organic solvents and also in the radiation curable composition.

According to one embodiment the blue dye comprises a terephthalate moiety and can thus be characterized as a terephthalate dye.

Suitable examples for the blue dye include Lumilux™ Blue (Honeywell) and Tinuvin™ 326 (Ciba).

The blue dye is typically present in the following amounts:
  Lower limit: at least 0.01 or at least 0.04 or at least 0.08 wt. %;
  Upper limit: utmost 0.1 or utmost 0.5 or utmost 1 wt. %;
  Range: from 0.01 to 1 or from 0.04 to 0.5 wt. % or from 0.08 to 0.1 wt. %;
  wt. % with respect to the weight of the curable composition.

The radiation curable composition described in the present text may also comprise stabilizer(s) as Component E.

A stabilizer may extend the shelf life of the curable composition, help prevent undesired side reactions, and adjust the polymerization process of the radiation curable component(s) present in the curable composition.

Adding one or more stabilizer(s) to the curable composition may further help to improving the accuracy or detail resolution of the surface of the 3-dim article to be produced.

In particular it was found that adding stabilizer(s) to the curable composition described in the present text may help to enhance the resolution and accuracy of the SLA process by attenuating or avoiding unwanted scattering effects, as well as increase the shelf life of the curable composition.

Stabilizer(s) which can be used often comprise a phenol moiety.

Specific examples of stabilizer(s) which can be used include: p-methoxyphenol (MOP), hydroquinone monomethylether (MEHQ), 2,6-di-tert-butyl-4-methyl-phenol (BHT; Ionol), phenothiazine, 2,2,6,6-tetramethyl-piperidine-1-oxyl radical (TEMPO) and mixtures thereof.

If present, the stabilizer(s) is present in the following amounts:

Lower amount: at least 0.001 or at least 0.005 or at least 0.01 wt. %;
Upper amount: at most 0.02 or at most 0.05 or at most 0.5 at most 1 wt. %;
Range: from 0.001 to 1 or from 0.005 to 0.05 wt. %;
wt. % with respect to the weight of the curable composition.

According to one embodiment, the radiation curable Composition I comprises:

Component A1 ((meth)acrylate): from 50 to 95 or from 55 to 90 wt. %;
Component A2 (urethane(meth)acrylate): from 0 to 40 or from 1 to 40 wt. %;
Component B (photoinitiator): from 0.01 to 5 or from 0.01 to 3 wt. %;
Component C (red, orange or yellow dye): from 0.001 to 1 or from 0.003 to 0.5 wt. %;
Component D (blue dye): from 0.01 to 1 or from 0.04 to 0.5 wt. %;
Component E (stabilizer): from 0.001 to 1 or from 0.005 to 0.05 wt. %;
wt. % with respect to the whole composition.

The composition described in the present text can be produced by mixing the respective components, in particular under save light conditions. If desired, a speed mixer can be used. Typically, Component A1 is provided first. The other components are added as desired.

During storage, the composition described in the present text is typically packaged in a suitable packaging device.

The curable composition described in the present text is typically stored in container. Suitable containers include vessels, foil bags, cartridges, etc.

The volume of the respective containers is not particularly limited, but is typically in a range from 10 to 200,000 ml or from 500 to 10,000 ml.

The curable Composition I described in the present text can also be provided as a kit of parts comprising the curable Composition I and an instruction of use.

The instruction of use typically describes under what conditions the curable composition should be used.

The radiation curable Composition I described in the present text can be used for producing a transparent 3-dim article.

The transparent 3-dim article obtained by curing the radiation curable Composition I can typically be characterized by the following features alone or in combination:

a) Tensile strength: from 0.5 to 50 MPa or from 1.0 to 30 MPa according to ISO/DIN 53504 (2015-8);
b) Elongation at break: from 10 to 1000% or from 50 to 500% according to ISO/DIN 53504 (2015-8);
c) Shore hardness A: from 30 to 90 according to ISO/DIN 53505 (2000-8);
d) Light transmission: at least 50% for a path length of 1 mm at using light having a wave length in the range of 450 to 600 nm;
e) Water contact angle: ≤100°;
f) Not sticky to surfaces of cured (meth)acrylates;
g) Color: red, orange, or yellow to the human eye.

The transparent 3-dim article is rubber-elastic and has a red color.

A combination of the features b) and d) or b), d) and e) or b), d), e) and f) can sometimes be preferred.

A water contact angle as outlined below can be beneficial in particular if the 3-dim article should be used as a mold in a moist or humid environment.

According to one embodiment, the transparent 3-dim article has the shape of an orthodontic or dental article.

According to one embodiment, the transparent 3-dim article is a dental article and has the shape of a dental impression.

The radiation curable Composition I described in the present text is in particular useful for producing a transparent, elastomeric 3-dim article by processing the radiation curable Composition I in an additive manufacturing process comprising a radiation curing step, in particular an SLA process.

As a result a transparent, elastomeric 3-dim article is obtained.

Such a process typically comprises the following steps:
providing a layer of the radiation curable composition on a surface,
radiation curing those parts of the layer of the radiation curable composition which will belong to the 3-dim article to be produced,
providing an additional layer of the radiation curable composition in contact with the radiation cured surface of the previous layer,
repeating the previous steps until a 3-dim article is obtained.

Such a process comprises the step of applying radiation to the surface of a radiation curable material, wherein the radiation is applied only to those parts of the surface which will later form a part of the article to be produced.

Radiation can be applied by using e.g. a laser beam or by mask-image projection. Using a mask-image projection based stereolithographie process (MIP-SL) is sometimes preferred, as it allows a more rapid manufacturing of the article.

A MIP-SL process can be described as follows:
i. A three-dimensional digital model of the article to be produced is provided.
ii. The three-dimensional digital model is sliced by a set of horizontal planes.
iii. Each thin slice is converted into a two-dimensional mask image.
iv. The mask image is then projected with the aid of a radiation source onto the surface of the radiation curable material being located in a building platform (e.g. having the shape of a vat).
v. The radiation curable material is only cured in those regions which are exposed.
vi. The building platform containing the radiation curable material or the layer of cured material is moved relative to the radiation source, wherein a new layer of radiation curable material is provided being in contact with the layer of the cured material produced in the previous step.

vii. Steps (iv) to (vi) are repeated until the desired article is formed.

Projecting the mask image on the radiation curable material can be done either top-down or bottom-up with respect to the orientation of the vat.

Using the bottom-up technique can be beneficial as less radiation curable material is needed.

It was found that the radiation curable composition described in the present text is in particular useful for processing it in a mask-image projection stereolithography process using the bottom-up projection technique.

The transparent 3-dim article has a particular shape and may act as mould, support or cover for a radiation curable Composition II being different from the radiation curable Composition I used for producing the transparent 3-dim article.

The radiation curable Composition II is cured by radiation, which is irradiated through the transparent 3-dim article produced from the radiation curable Composition I.

In particular the process can be described as follows:

The process comprising the steps of
a) providing the radiation curable Composition I described in the present text,
b) processing the radiation curable Composition I in an additive-manufacturing process using radiation for curing the composition to obtain a transparent 3-dim article having an outer and an inner side,
c) placing a radiation curable Composition II on the inner side of the transparent 3-dim article,
d) light curing the radiation curable Composition II by irradiating light from the outer side of the transparent 3-dim article,
e) optionally removing the transparent 3-dim article from the light cured Composition II.

The radiation curing step b) and light curing step d) are typically done at different wave lengths.

The radiation curing step b) is typically done within a wave length range from 350 to 420 nm.

The light curing step d) is typically done within a wave length range from 430 to 500 nm.

The radiation curable Composition II is different from the radiation curable Composition I used for producing the transparent 3-dim article.

The radiation curable Composition II typically differs from radiation curable Composition I in the following features alone or in combination:
 amount and nature of (meth)acrylate components;
 filler content;
 opacity;
 viscosity.

The radiation curable Composition II typically comprises
 radiation curable components, in particular radiation curable components comprising (meth)acrylate moieties,
 photoinitiator(s), in particular, photoinitiator(s) comprising an alpha-diketon moiety,
 optionally filler(s).

Examples of photoiniators comprising an alpha-diketon moiety include moieties selected from from benzophenone, xanthone or quinone.

Examples include camphorchinone, benzil, furil, 3,3,6,6-tetramethylcyclohexanedione, phenanthraquinone and 1-phenyl-1,2-propandion.

Such photoinitiator(s) are typically used in combination with an aliphatic amine.

According to one embodiment the radiation curable composition B is selected from a dental cement, a dental adhesive or a dental (flowable) composite.

An example of a suitable dental cements is described in U.S. Pat. No. 8,236,871 B2 (Hecht et al.).

The invention is also directed to a process of producing a transparent positioning tray, the process comprising the steps of
 providing the radiation curable Composition I described in the present text,
 providing a personalized data set relating to at least one part of the dental situation of a patient,
 using the personalized data set for the processing of the radiation curable Composition I in an additive-manufacturing process comprising a radiation step to obtain a 3-dim article having the shape of a transparent positioning tray having an outer surface and an inner surface, the inner surface corresponding to the surface of the dental situation, The process may further comprise the step of placing orthodontic brackets in contact with the inner surface of the 3-dim article. The orthodontic brackets typically comprise a layer of a radiation curable composition.

The invention is also directed to a process of fixing orthodontic brackets to the surface of teeth in the mouth of a patient.

Such a process may further comprise the step of placing the transparent positioning tray containing the orthodontic brackets in the mouth of the patient.

The process may further comprise the step of irradiating light from the outer surface of the transparent positioning tray to the orthodontic brackets comprising a layer of radiation curable composition.

This process step typically causes the curing of the radiation curable composition located on orthodontic brackets and thereby fixing the orthodontic brackets to the surface of the tooth belonging to the dental situation.

The process may further comprise the step of removing the transparent positioning tray from the mouth of the patient.

The invention also relates to a kit of parts comprising
 the radiation curable Composition I described in the present text, being radiation curable by applying radiation having a wavelength in the range of 350 to 420 nm and
 a radiation curable Composition II being different from the radiation curable Composition I and being radiation curable by applying radiation having a wavelength in the range of 420 to 500 nm.

Such a kit of parts is in particular useful for producing 3-dim cured articles based on the radiation curable composition II with the aid of radiation curable composition I from which a transparent mould or transparent cover has been produced by means of an additive manufacturing process.

According to one embodiment, the kit comprises
 the radiation curable composition I described in the present text typically contained in a packaging device and
 orthodontic brackets comprising a layer of a radiation curable dental adhesive or cement.

All components used in the dental composition of the invention should be sufficiently biocompatible, that is, the composition should not produce a toxic, injurious, or immunological response in living tissue.

The radiation curable Composition I described in the present text does typically not comprise the following component(s) alone or in combination:
 cationically curable component(s) in an amount of more than 5 wt. %;

organic or inorganic pigment(s) in an amount of more than 1 wt. % or more than 0.1 wt. %;

filler particles having a refractive index which differs by more than 0.5 from the refractive index of the matrix in an amount of more than 5 wt. %;

wt. % with respect to the whole composition.

Thus, the curable composition described in the present text is essentially free of either or all of the above components.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate the invention.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Methods

Viscosity

If desired, the viscosity can be measured using a Physica Rheometer MCR 301 device with a plate-plate system (diameter 20 mm) and a slit of 0.2 mm. The viscosity values (Pas) can be recorded at 23° C. for each shear rate (starting from 10 l/s to 100 l/s).

Method for Determining pH-Value

If desired, the measurement of the pH-value can be achieved by means known by the person skilled in art. E.g. the resin can be dispersed in de-ionized water and an instrument like Metrohm™ 826 can be used.

Method for Determining Light Transmission

If desired, the light transmission (contrast ratio mode) can be measured using a Color i7 spherical spectrophotometer (available from x-rite Inc., Grand Rapids, Mich., USA).

The test specimen is printed in the shape of a cylinder with approximate dimensions: diameter of 30±0.5 mm and thickness of 1±0.05 mm and processed as described in the present text.

For the measurement, the spectrometer parameters are: D65 illuminant (light source; day light; 6,500 K) and 10° observer. The white and black background is determined as followed: for the black background the sphere is closed and thereby no light is detected by the sensors of the Color i7. As white (or 100% D65 light) a measurement, without anything between sphere and sensors of the Color i7, is necessary. For measurement of the sample, the specimen is placed with a sample holder between sphere and lens of the Color i7. The specimen is thereby directly placed onto the aperture of the sphere.

Transmission (% T) is calculated using the Software Color iControl V7.5.10 at 450, 470 and 500 nm wavelength.

Method for Determining Light Absorption Bands

If desired, the light absorption spectrum can be determined by using a spectrophotometer Spectramax 190 (available from Molecular Devices LLC., Sunnyvale, Calif., USA). As cuvette a multicuvette is used like Microtest 96-Well 370 µl Clear Plate (available from BD Biosciences Franklin Lakes, N.J., USA). 200 µl of mentioned resin solutions are placed into one of the 96 cuvettes and put into the Spectromax 190. The spectrum is recorded between 200 nm and 800 nm in 1 nm steps.

Additive Manufacturing Process

Compositions were used (VAT-polymerization) in a DLP/SLA 3D-printer (Rapid Shape S30) at room temperature (23° C.) and 50% humidity to produce test specimen to check the detail accuracy of the resulting printed elastomers.

The following parameters were applied:

light polymerization using an LED-lamp: 405 nm, 50 mW/cm$^2$, separation gap: 2.5 mm, light exposure time: from 20 to 0.5 s, layer thickness 50 µm.

Post Processing

The specimens were cleaned in an ultrasonic bath filled with iso-propanol for 5 min and post-processed using a Visio™ Beta apparatus (3M Oral Care) applying program 2 without vacuum for 7 min.

Method for Determining Detail Accuracy

The printing accuracy can be determined by visually inspecting the obtained 3-dim articles by using the following protocol. The 3-dim articles were inspected in normal room lighting in front of a white background (regular white printing paper) using Binocular magnifiers for spectacles at a magnification of 2.75× (Fa. Fino).

| Rating | Criteria |
| --- | --- |
| ++ | All structures and every detail very good visible, very good contrast and/or opacity. |
| + | All structures and details visible, contrast and/or opacity sufficient. |
| − | Structures visible, details partially not clearly visible, contrast and/or opacity too low. |
| −− | Structures and details not clearly visible, contrast and/or opacity not sufficient. |

Shore Hardness

The Shore hardness can be determined according to DIN 53505 (2000-8) 24 hours after curing of the specimens. Specimens are prepared by filling the formulations into a metal mold (cylindrical 15×6 mm) covered with plastic foil sheets, pressed and cured in a Visio™ Beta (3M) device with program 2 without vacuum.

Tensile Strength and Elongation at Break

To determine the tensile strength and elongation, the formulations are filled in a metal mold (2×2×25 mm) covered with plastic foil sheets, pressed and cured in a Visio™ Beta (3M) device with program 2 without vacuum. Test procedures follow DIN 53505 (2015-8)

Water Contact Angle

If desired, the water contact angle can be determined as described in on page 40 of WO 2014/130603 (3M).

Stickiness

A mold was prepared by light curing the material after it was applied over a tooth in a dental model using a conventional Elipar™ S 10 light curing device (max. peak 450 nm; 3M Oral Care) with 20 sec curing time.

The mold was then filled with a light curable cement RelyX™ Unicem 2 Automix (A2) (3M Oral Care).

Immediately after that, the cement in the mold was exposed to the light of the Elipar™ S10 through the red mold for 20 sec. This resulted in an immediate cure of the RelyX™ Unicem 2 material which indicates good curability of the cement through the cured elastomer.

The stickiness can be determined by visually and manually inspecting the adhesion of a sample of a light-cured material X in a mold consisting of light-cured composition Y.

| Rating | Criteria |
|---|---|
| ++ | X can be removed from the mold Y without tear-offs on the surface of Y. |
| + | X can be removed from the mold Y. The mold Y is not destroyed by that but there are single tear offs in the structure of the surface. |
| − | X and Y show a significant adhesion. X can be removed from the mold but there are severe tear-offs in Y which partially destroy the surface of Y. |
| −− | X and Y show chemical bonding to each other. The mold must be destroyed to remove X. |

Materials

TABLE 1

| Name | Description |
|---|---|
| Irgacure ™ 819 | Photo initiator; phosphine oxide, CAS 162881-26-7 |
| Lumilux ™ Blau LZ | Blue dye |
| Fluoreszenzrot 94720 | Red Perylene Dye, Kremer Pigments |
| Fluoreszenzgelb 94700 | Yellow Perylene dye, Kremer Pigments |
| Fluoreszenzorange 94738 | Orange Perylene dye, Kremer Pigments |
| Diurethanedimethacrylate | CAS: 72869-86-4; |
| DIOL-6000-DMA | α-ω-methacrylated copolymer of ethyleneoxide/THF; M(w) about 6,000 |
| Dibenzyltoluene | Plasticizer, CAS: 26898-17-9 |
| Hydrochinonmono-methylether | Stabilizer, CAS: 150-76-5 |

Preparation of Compositions

All compositions were manufactured by combining the respective components and stirring the composition using a magnetic stirrer for 2 hours.

Compositions

All amounts are given in parts by weight.

|  | Comp. 1 | Comp. 2 | Comp. 3 | Comp. 4 | Comp. 5 |
|---|---|---|---|---|---|
| DIOL-6000-DMA | 92.44 | 92.47 | 74.59 | 74.59 | 74.59 |
| Diurethanedimethacrylate | 5.10 | 5.05 | 20.0 | 20.0 | 20.0 |
| Irgacure ™ 819 | 0.21 | 0.20 | 0.20 | 0.20 | 0.20 |
| Red Perylene Dye | 0.01 | 0.00 | 0.01 | — | — |
| Yellow Perylene Dye | — | — | — | 0.01 | — |
| Orange Perylene Dye | — | — | — | — | 0.01 |
| Lumilux Blau LZ | 0.20 | 0.20 | 0.20 | 0.20 | 0.20 |
| Hydrochinonmono-methylether | 0.05 | 0.05 | — | — | — |
| Dibenzyltoluene | 1.99 | 2.02 | 5.00 | 5.00 | 5.00 |

Results

Example 1

Characterization of Composition 1 and 2 Before Processing

|  | Composition 1 | Composition 2 |
|---|---|---|
| Viscosity at 20 1/s | 12 | 12 |
| Viscosity at 95 1/s | 12 | 12 |
| Color | red | colorless |

Characterization of Composition 1 and 2 after Curing and Post-Processing

|  | Composition 1 | Composition 2 |
|---|---|---|
| Tensile strength | 1.5 MPa | 1.5 MPa |
| Elongation at break | 66% | 63% |
| Shore hardness A | 59 | 58 |
| Detail accuracy | + | −− |

Figure 2:
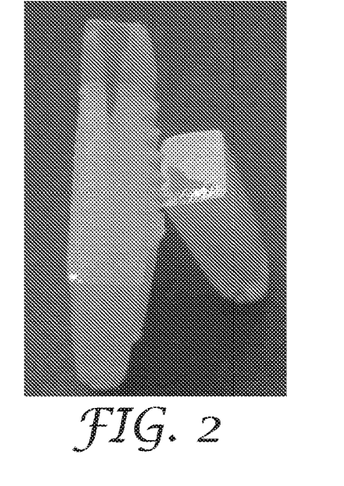
FIG. 2 shows a picture of a test specimen obtained from the coloured radiation curable composition described in the present text.
Figure 3:
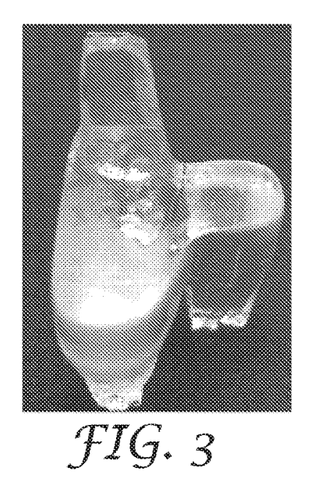
FIG. 3 shows a picture of a test specimen obtained from a non-coloured radiation curable composition.

Composition 1 achieved satisfactory resolution without significant over-curing (FIG. 2). Composition 2 showed unacceptable over-curing under the same conditions (FIG. 3).

Example 2

Characterization of Compositions 3, 4 and 5 Before Processing

|  | Composition 3 | Composition 4 | Composition 5 |
|---|---|---|---|
| Viscosity at 20 1/s | 10 Pa*s | 9 Pa*s | 10 Pa*s |

Characterization of Compositions 3, 4 and 5 after Curing and Post-Processing

|  | Composition 3 | Composition 4 | Composition 5 |
|---|---|---|---|
| Tensile strength | 4.1 MPa | 4.1 MPa | 4.7 MPa |
| Elongation at break | 76% | 73% | 84% |
| Shore hardness A | 78 | 78 | 79 |
| Detail accuracy | ++ | ++ | ++ |
| Stickiness | ++ | ++ | ++ |
| Light Transmission at 500 nm wavelength | app. 69% | app. 92% | app. 40% |

Example 3

A sample of a clear positioning tray (CPT) was produced using an STL-file using formulation from Composition 3.

Production, post-processing and cleaning were conducted according to the procedure in Example 2.

Figure 4:
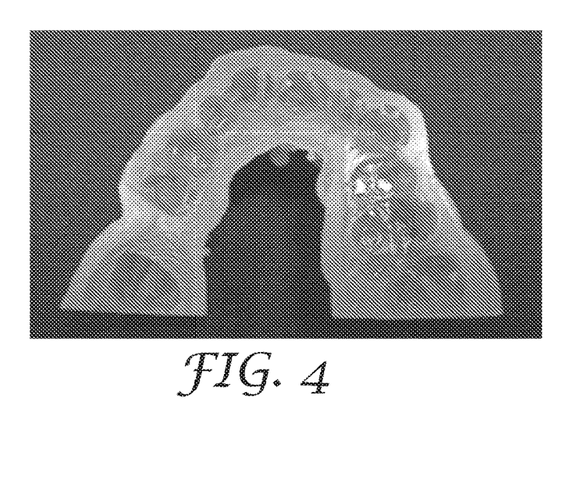
FIG. 4 shows a picture of a clear positioning tray obtained from the coloured radiation curable composition described in the present text.

The result is shown in FIG. 4. The CPT showed very high detail accuracy (++) when inspected visually.

The invention claimed is:

1. A radiation curable composition for additive-manufacturing processes, the composition comprising:
   a (meth)acrylate component(s) not comprising a urethane moiety moiety as Component A1,
     the (meth)acrylate component(s) comprising a polyether backbone to which (meth)acrylate moieties are attached and the (meth)acrylate component(s) characterized by a molecular weight Mw of at least 1,000 g/mol;
   photo initiator as Component B;
   a red dye, a yellow dye, an orange dye, or combination thereof as Component C, the red dye, the yellow dye, and the orange dye comprising a perylene moiety;
   a blue dye as Component D,
     the blue dye comprising a terephthalate moiety, and
     the blue dye characterized by having a light absorption band in the range of 350 to 420 nm; and
   optionally stabilizer as Component E.

2. The radiation curable composition according to claim 1, the composition being characterized by the following features alone or in combination:
   viscosity: less than 200 Pa*s at 23° C.;
   pH value: 6 to 8;
   light transmission: at least 40% for a path length of 1 mm using light having a wave length of 500 nm;
   radiation curable with light having a wavelength in the range of 350 to 420 nm;
   appearance: transparent;
   color: red, yellow or orange.

3. The radiation curable composition according to claim 1, the (meth)acrylate component(s) being characterized by the following features alone or in combination:
   comprising at least 2 (meth)acrylate moieties;
   molecular weight (Mw): from 1,000 to 20,000 g/mol;
   viscosity: from 0.1 to 100 Pa*s at 23° C.

4. The radiation curable composition according to claim 1, the red, orange or yellow dye being characterized by the following features alone or in combination:
   solubility: soluble in triethylenglycoldi(meth)acrylate at 23° C.;
   having a light absorption band in the range of 460 to 600 nm.

5. The radiation curable according to claim 1, the blue dye being characterized by the following features alone or in combination:
   solubility: soluble in triethylenglycoldi(meth)acrylate at 23° C.

6. The radiation curable composition according to claim 1, the composition comprising in addition (meth)acrylate component(s) comprising an urethane moiety as Component A2, wherein Component A1 is present in a higher amount compared to Component A2.

7. A process of producing an elastomeric 3-dim article, the process comprising the step of processing the radiation curable composition described in claim 1 in an additive-manufacturing process comprising a radiation curing step using light with a wave length in the range from 350 to 420 nm.

8. The process of claim 7, the elastomeric 3-dim article having the shape of an orthodontic or dental article, the dental article having the shape of a dental impression.

9. An elastomeric 3-dim article comprising the radiation curable composition as described in claim 1 in its cured state.

10. The elastomeric 3-dim article of claim 9 being characterized by the following features alone or in combination:
    Tensile strength: from 0.5 to 50 MPa according to ISO/DIN 53504 (2015-8);
    Elongation at break: from 10 to 1000% according to ISO/DIN 53504 (2015-8);
    Shore hardness A: from 30 to 90 according to ISO/DIN 53505 (2000-8);
    Light transmission: at least 50% for a path length of 1 mm at using light having a wave length in the range of 450 to 600 nm
    Water contact angle: ≤100°;
    Not sticky to surfaces of cured (meth)acrylates;
    Color: red, orange or yellow.

11. A process of curing a radiation curable Composition II, the process comprising the steps of:
    a) providing a radiation curable Composition I, the radiation curable Composition I being the radiation curable composition as described in claim 1, b) processing the radiation curable Composition I in an additive-manufacturing process using radiation for curing the Composition I to obtain a transparent elastomeric 3-dim article having an outer side and an inner side, c) placing the radiation curable Composition II on the inner side of the transparent elastomeric 3-dim article, d) light curing the radiation curable Composition II from the outer side of the transparent elastomeric 3-dim article
    the radiation curable Composition II being different from the radiation curable Composition I, the radiation curable Composition II comprising (meth)acrylate moieties, photo-initiator(s) and optionally filler(s).

12. The process of claim 11, wherein the curing in step b) and step d) is done at different wave lengths.

13. The process of claim 11,
    the radiation curing step b) being done at a wave length in the range from 350 to 420 nm,
    the radiation curing step d) being done at a wave length in the range from 430 to 500 nm.

14. The process of claim 11, the radiation curable Composition II being selected from a dental cement, a dental adhesive, or a dental composite material.

15. A kit of parts comprising:
    a radiation curable Composition I, the radiation curable Composition I being the radiation curable composition as described in claim 1, and
    a radiation curable Composition II being different in its chemical composition from the radiation curable Composition I and being radiation curable within a wavelength in the range of 430 to 500 nm.

* * * * *